United States Patent
Sun et al.

(10) Patent No.: US 10,997,719 B2
(45) Date of Patent: May 4, 2021

(54) METHOD OF OBTAINING MEDICAL SAGITTAL IMAGE, METHOD OF TRAINING NEURAL NETWORK AND COMPUTING DEVICE

(71) Applicant: NATIONAL CHENG KUNG UNIVERSITY, Tainan (TW)

(72) Inventors: Yung-Nien Sun, Tainan (TW); Pei-Yin Tsai, Tainan (TW); Chia-Ju Hsieh, Tainan (TW); Shih-Ting Huang, Tainan (TW); Yu-Han Huang, Tainan (TW)

(73) Assignee: National Cheng Kung University, Tainan (TW)

( * ) Notice: Subject to any disclaimer, the term of this patent is extended or adjusted under 35 U.S.C. 154(b) by 74 days.

(21) Appl. No.: 16/368,412

(22) Filed: Mar. 28, 2019

(65) Prior Publication Data
US 2020/0211179 A1 Jul. 2, 2020

(30) Foreign Application Priority Data

Dec. 28, 2018 (TW) ................. 10714777.4

(51) Int. Cl.
*G06T 7/00* (2017.01)
*G06T 7/70* (2017.01)
*G06T 19/20* (2011.01)

(52) U.S. Cl.
CPC .............. *G06T 7/0012* (2013.01); *G06T 7/70* (2017.01); *G06T 19/20* (2013.01);
(Continued)

(58) Field of Classification Search
CPC . G06T 2207/20081; G06T 2207/20084; G06T 7/0012; G06T 7/11; G06T 2207/10081; G06T 2207/10088; G06T 2207/30004; G06T 7/143; G06T 2207/10072; G06T 2207/20021; G06T 2207/20076; G06T 2207/30012; G06T 2207/30096; G06T 7/337; G06T 11/003; G06T 11/005; G06T 19/20; G06T 2200/04; G06T 2207/10012
See application file for complete search history.

(56) References Cited

U.S. PATENT DOCUMENTS 10,140,544 B1 * 11/2018 Zhao ................... G06T 7/143
2018/0061059 A1 * 3/2018 Xu ....................... G06N 3/084
(Continued)

FOREIGN PATENT DOCUMENTS

CN           104414680 A      3/2015

*Primary Examiner* — Golam Sorowar
(74) *Attorney, Agent, or Firm* — Muncy, Geissler, Olds & Lowe, P.C.

(57) ABSTRACT

A method of training neural network for obtaining medical sagittal image includes: using a first neural network on a 3-D medical image to generate a prediction sagittal mask; generating a prediction result according to the 3-D medical image and the prediction sagittal mask; generating a ground truth result according to the 3-D medical image and a ground truth sagittal mask; using a second neural network on the prediction result and the ground truth result; generating a loss function data according to an output of the second neural network; and adjusting parameters of the first neural network or the second neural network according to the loss function data.

14 Claims, 9 Drawing Sheets

(52) U.S. Cl.
CPC ............... *G06T 2207/10081* (2013.01); *G06T 2207/10088* (2013.01); *G06T 2207/10116* (2013.01); *G06T 2207/10136* (2013.01); *G06T 2207/20081* (2013.01); *G06T 2207/20084* (2013.01); *G06T 2207/30044* (2013.01); *G06T 2219/008* (2013.01); *G06T 2219/2016* (2013.01)

(56) References Cited

U.S. PATENT DOCUMENTS

| | | | |
|---|---|---|---|
| 2018/0286050 A1* | 10/2018 | Cheng | G06T 7/11 |
| 2019/0192880 A1* | 6/2019 | Hibbard | A61N 5/1039 |
| 2019/0216409 A1* | 7/2019 | Zhou | A61B 6/032 |
| 2019/0362522 A1* | 11/2019 | Han | G06T 11/008 |

* cited by examiner

METHOD OF OBTAINING MEDICAL SAGITTAL IMAGE, METHOD OF TRAINING NEURAL NETWORK AND COMPUTING DEVICE

CROSS REFERENCE TO RELATED APPLICATIONS

This Non-provisional application claims priority under 35 U.S.C. § 119(a) on Patent Application No(s). 107147774 filed in Taiwan, Republic of China on Dec. 28, 2018, the entire contents of which are hereby incorporated by reference.

BACKGROUND

Technology Field

The present disclosure relates to a neural network and a computing device. In particular, the present disclosure relates to a neural network for medical sagittal images and a computing device thereof.

Description of Related Art

Medical examination equipment includes ultrasound examination equipment, computed tomography and the likes. Taking prenatal examination for monitoring fetal growth as an example, the ultrasound examination plays a very important role in prenatal diagnosis. Physicians can measure the zona pellucida of the fetal neck and growth parameters according to the ultrasound image of the first trimester as a screening for early Down's syndrome, fetal genetic defects or hypoplasia. However, the fetal ultrasound images usually have many shortcomings such as noises and boundary blur. Moreover, the ultrasound image of the first trimester is more complicated because the fetal development is not complete and the fetal itself is attached to the endometrium, causing the boundary to be inconspicuous. Accordingly, the ultrasound image measurement and evaluation mostly relies on the experience of professional clinical personnel, and is also prone to human error. In addition, the thickness of the zona pellucida of the fetal neck needs to be measured on the middle sagittal plane (MSP). However, how to find this correct observation in the ultrasound image is a time-consuming and difficult technique.

Therefore, it is an important subject to provide a neural network and a computing device that can find the correct sagittal plane for measurement.

SUMMARY

In view of the foregoing, an objective of this disclosure is to provide a neural network, a related method and a computing device that can find the correct sagittal plane for measurement.

This disclosure provides a method of training a neural network for obtaining a medical sagittal image, comprising: using a first neural network on a 3-D medical image to generate a prediction sagittal mask; generating a prediction result according to the 3-D medical image and the prediction sagittal mask; generating a ground truth result according to the 3-D medical image and a ground truth sagittal mask; using a second neural network on the prediction result and the ground truth result; generating a loss function data according to an output of the second neural network; and adjusting parameters of the first neural network or the second neural network according to the loss function data.

In one embodiment, the 3-D medical image is an ultrasound image, a computed tomography image, a panoramic X-ray image, or a magnetic resonance image.

In one embodiment, the prediction result is generated according to a combining calculation of the 3-D medical image and the prediction sagittal mask, and the ground truth result is generated according to a combining calculation of the 3-D medical image and the ground truth sagittal mask.

In one embodiment, the first neural network is a convolutional neural network comprising a plurality of convolution layers, a flatten layer, a reshaping layer, and a plurality of deconvolution layers.

In one embodiment, the second neural network is a convolutional neural network comprising a plurality of convolution layers and a flatten layer.

In one embodiment, the first neural network and the second neural network are a generative adversarial network.

In one embodiment, the loss function data comprises a first loss function data and a second loss function data. The first loss function data is used for adjusting the first neural network, and the second loss function data is used for adjusting the second neural network.

In one embodiment, the training method further comprises: creating the 3-D medical image according to a plurality of 2-D medical images.

In one embodiment, the training method further comprises: generating a 2-D sagittal image according to the prediction sagittal mask and the 3-D medical image.

This disclosure also provides a method of obtaining a medical sagittal image, comprising: using a first neural network on a 3-D medical image to generate a prediction sagittal mask; and generating a 2-D sagittal image according to the 3-D medical image and the prediction sagittal mask.

In one embodiment of the method of obtaining a medical sagittal image, the step of generating the 2-D sagittal image comprises: generating a sagittal description data; and converting a coordinate of the 3-D medical image according to the sagittal description data to generate the 2-D sagittal image.

In one embodiment of the method of obtaining a medical sagittal image, the 3-D medical image is an ultrasound image, a computed tomography image, a panoramic X-ray image, or a magnetic resonance image.

In one embodiment of the method of obtaining a medical sagittal image, the first neural network is a convolutional neural network comprising a plurality of convolution layers, a flatten layer, a reshaping layer, and a plurality of deconvolution layers.

In one embodiment of the method of obtaining a medical sagittal image, the method further comprises: creating the 3-D medical image according to a plurality of 2-D medical images.

This disclosure further provides a computing device for performing the above-mentioned method.

In one embodiment, the computing device comprises a processing core and a storage unit. The storage unit stores the program code for executing the above-mentioned method, and the processing core is coupled with the storage unit and executes the program code for performing the above-mentioned method.

As mentioned above, in the method of training a neural network for obtaining a medical sagittal image, the method of obtaining a medical sagittal image, and the computing device of this disclosure, the neural network is used for detecting the sagittal plane (e.g. the middle sagittal plane (MSP) of fetal from the ultrasound image). The neural network can be used as a filter for learning the feature points in the medical image and the spatial position thereof, and generating a 3-D mask containing the plane position information. After the post-processing (conversion), the desired image of the middle sagittal plane can be obtained.

BRIEF DESCRIPTION OF THE DRAWINGS

The disclosure will become more fully understood from the detailed description and accompanying drawings, which are given for illustration only, and thus are not limitative of the present disclosure, and wherein.

DETAILED DESCRIPTION OF THE DISCLOSURE

The present disclosure will be apparent from the following detailed description, which proceeds with reference to the accompanying drawings, wherein the same references relate to the same elements.

Figure 1:
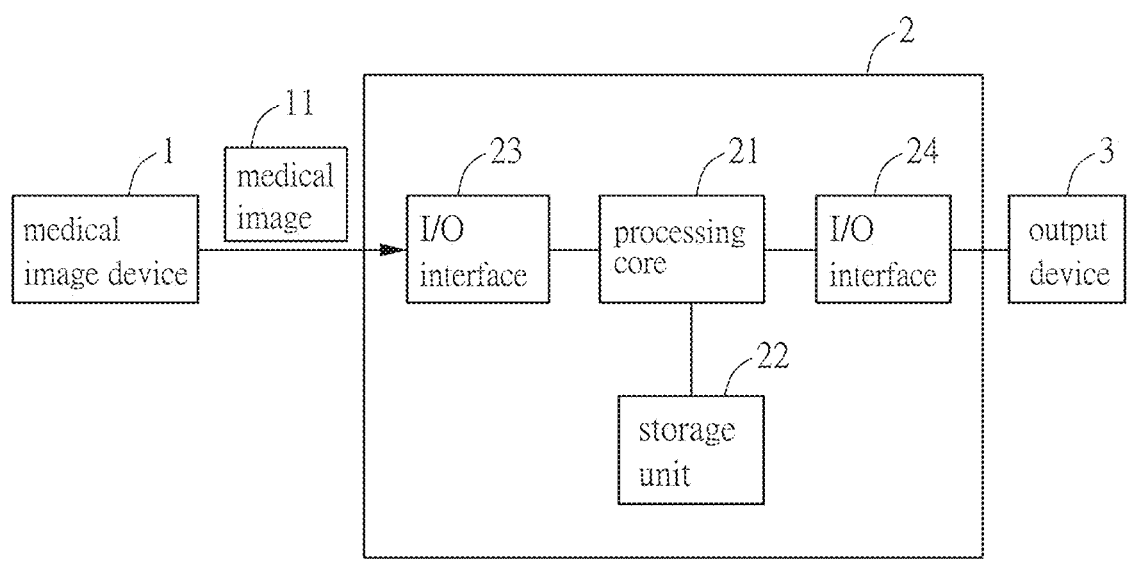
FIG. 1 is a block diagram of a system for processing the medical sagittal image according to an embodiment of this disclosure.

FIG. 1 is a block diagram of a system for processing the medical sagittal image according to an embodiment of this disclosure. As shown in FIG. 1, the system comprises a medical image device 1, a computing device 2 and an output device 3. The computing device 2 comprises a processing core 21, a storage unit 22 and a plurality of input/output (I/O) interfaces 23 and 24. The processing core 21 is coupled with the storage unit 22 and the input/output interfaces 23 and 24. The input/output interface 23 is configured to receive the medical image 11 generated by the medical image device 1, and the input/output interface 24 is communicated with the output device 3. The computing device 2 can output the processing result to the output device 3 through the input/output interface 24.

The storage unit 22 stores the program code to be executed by the processing core 21. The storage unit 22 includes a non-volatile memory and/or a volatile memory, such as a hard disk, a flash memory, a solid state disk, a compact disk, or the likes. The volatile memory is, for example, a dynamic random access memory, a static random access memory, or the likes. For example, the program code is stored in the non-volatile memory, and the processing core 21 can load the program code from the non-volatile memory into the volatile memory and then execute the loaded program code.

The processing core 21 is, for example, a processor, a controller, or the likes. The processor includes one or more cores. The processor can be a central processing unit or a graphics processor. In addition, the processing core 21 can also be the core of a processor or a graphics processor. On the other hand, the processing core 21 can also be a processing module, which includes a plurality of processors such as a central processing unit and a graphics processor.

The medical image device 1 can generate a medical image 11, and it can be, for example, an ultrasound inspection device, a computed tomography device, a panoramic X-ray device, or a magnetic resonance device. The medical image 11 generated by the medical image device 1 can be first transmitted to a storage medium and then input from the storage medium to the input/output interface 23. The input/output interface 23 is, for example, a peripheral transmission port, and the storage medium is, for example, a non-volatile memory. In addition, the medical image device 1 may be wired or wirelessly connected to the input/output interface 23, and the medical image 11 may be transmitted from the medical image device 1 to the input/output interface 23 via the wired or wireless connection therebetween. The input/output interface 23 may be, for example, a communication port.

The computing device 2 can perform the method of training a neural network for obtaining a medical sagittal image. The storage unit 22 stores the related program code of the training method, the models and trained parameters, and the processing core 21 executes the program code to perform the training method. The training method comprises the following steps of: using a first neural network on a 3-D medical image to generate a prediction sagittal mask; generating a prediction result according to the 3-D medical image and the prediction sagittal mask; generating a ground truth result according to the 3-D medical image and a ground truth sagittal mask; using a second neural network on the prediction result and the ground truth result; generating a loss function data according to an output of the second neural network; and adjusting parameters of the first neural network or the second neural network according to the loss function data.

In addition, the computing device 2 can perform the method of obtaining a medical sagittal image. The storage unit 22 stores the related program code of the obtaining method, the models and used parameters, and the processing core 21 executes the program code to perform the obtaining method. The method of obtaining a medical sagittal image comprises the following steps of: using a first neural network on a 3-D medical image to generate a prediction sagittal mask; and generating a 2-D sagittal image according to the 3-D medical image and the prediction sagittal mask.

The output device 3 is a device having an image output ability, such as a display, a projector, a printer, or the likes. The computing device 2 performs a method of obtaining a medical sagittal image to output the generated 2-D sagittal image to the output device 3.

The first neural network is a neural network treated by the method of training a neural network for obtaining a medical sagittal image. The sagittal detection is regarded as a filter for filtering the sagittal plane from the 3-D medical image so as to generate a 3-D binary mask. The filtered information not only remains the features that are needed on the sagittal plane, but also has the location information. Using the trained first neural network, a plane can be found from the spatial volume of the 3-D medical image to accurately cut the object in the image into left and right halves that still have the needed features. Compared with the intuitive method of listing all candidate slices and classifying these slices, the method of the present disclosure overcomes the shortcomings of the above-mentioned intuitive method which is very time consuming and inefficient, and overcomes the distortion problem of the intuition method that only uses the 2-D image as a basis for judging the true position in the 3-D space.

Figure 2A:
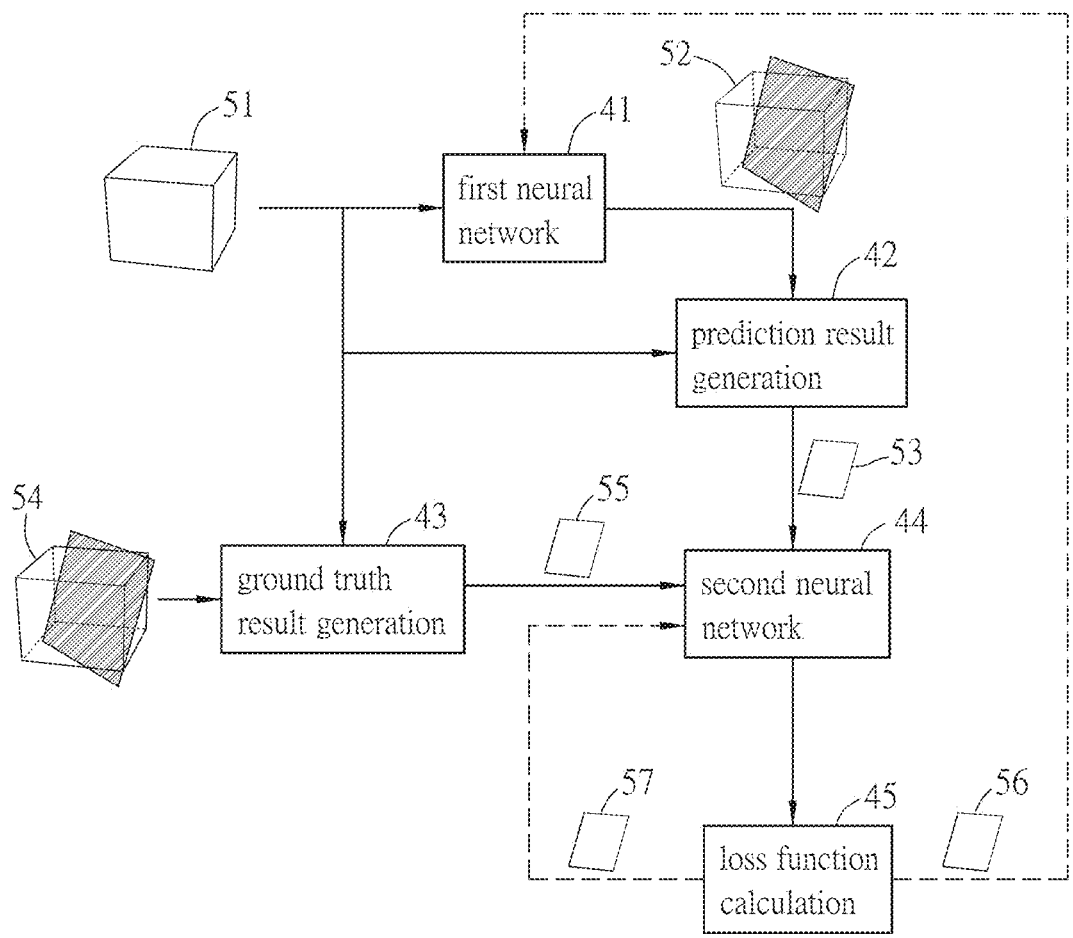
FIG. 2A is a block diagram showing a method of training a neural network for obtaining a medical sagittal image according to an embodiment of this disclosure.

FIG. 2A is a block diagram showing a method of training a neural network for obtaining a medical sagittal image according to an embodiment of this disclosure. As shown in FIG. 2A, the program codes and information for implementing the first neural network 41, the prediction result generation 42, the ground truth result generation 43, the second neural network 44, and the loss function calculation 45 can be stored in the storage unit 22 of FIG. 1, and the processing core 21 can execute and process the program codes and information. The 3-D medical image 51, the prediction sagittal mask 52, the prediction result 53, the ground truth sagittal mask 54, the ground truth result 55, and the loss function data 56 and 57 can be stored in or loaded into the storage unit 22, and provided for the processing step of the processing core 21.

The first neural network 41 is used on the 3-D medical image 51 to generate the prediction sagittal mask 52. The prediction result generation 42 can obtain the prediction result 53 according to the 3-D medical image 51 and the prediction sagittal mask 54. The ground truth result generation 43 can generate the ground truth result 55 according to the 3-D medical image 51 and the ground truth sagittal mask 54. The second neural network 44 is used on the prediction result generation 42 and the ground truth result generation 43 to generate an output. The loss function calculation 45 can generate the loss function data 56 and 57 according to the output of the second neural network 44 by utilizing a loss function, and then adjust the parameters of the first neural network 41 or the second neural network 44 according to the loss function data 56 and 57.

The training method can use the deep learning technology to automatically detect the sagittal plane. For example, the first neural network 41 and the second neural network 44 can be two sub-network portions of a generative adversarial network. For example, the first neural network 41 functions as a generator, and the second neural network 44 functions as a critic. The output loss of the critic can be used to adjust or optimize the generator and the critic.

The 3-D medical image 51 is an inputted image. For example, the 3-D medical image can be an ultrasound image, a computed tomography image, a panoramic X-ray image, or a magnetic resonance image. The ultrasound image is, for example, a whole body ultrasound image or a local ultrasound image, such as a head ultrasound image, a neck ultrasound image, a head and neck ultrasound image, or any of ultrasound images of other parts. The 3-D medical image 51 can be the medical image 11 generated by the medical image device 1 of FIG. 1. That is, the medical image 11 itself is a 3-D image. Alternatively, the 3-D medical image 51 can be generated according to the medical image 11. For example, the medical image 11 includes multiple 2-D images, which represent different sections of the target object or the target object at different coordinate planes, and then the 3-D medical image 51 can be created according to the multiple 2-D images.

The first neural network 41 can take the 3-D medical image 51 as an input and process it, and the processed result can function as the prediction sagittal mask 52. For example, the first neural network 41 can be designed as a filter, which can learn the feature points in the 3-D medical image 51 and the spatial position thereof, and generating a 3-D prediction sagittal mask 52 containing the plane position information. The dimension and scale of the prediction sagittal mask 52 can be the same as those of the 3-D medical image 51.

The first neural network 41 can retrieve the cropped volume from the 3-D medical image 51 as the input, and output the 3-D mask to provide the prediction sagittal mask 52. The 3-D mask can be, for example, a 3D binary mask. The input and output of the first neural network 41 have the same dimensions and scales. The position information of the sagittal plane is embedded in the 3-D mask. If the voxel is located on the sagittal plane, the corresponding mask value is 1, and if the voxel is excluded from the sagittal plane, the corresponding mask value is 0.

The prediction result generation 42 can generate the prediction result 53 according to the 3-D medical image 51 and the ground truth sagittal mask 54, and the generating method can be, for example, a combining calculation. The ground truth result generation 43 can generate the ground truth result 55 according to the 3-D medical image 51 and the ground truth sagittal mask 54, and the generating method can be, for example, a combining calculation. The ground truth sagittal mask 54 and the 3-D medical image 51 can have the same dimensions and scales. In a preferred embodiment, the 3-D medical image 51, the prediction sagittal mask 52, and the ground truth sagittal mask 54 have the same dimensions and scales.

Figure 2B:
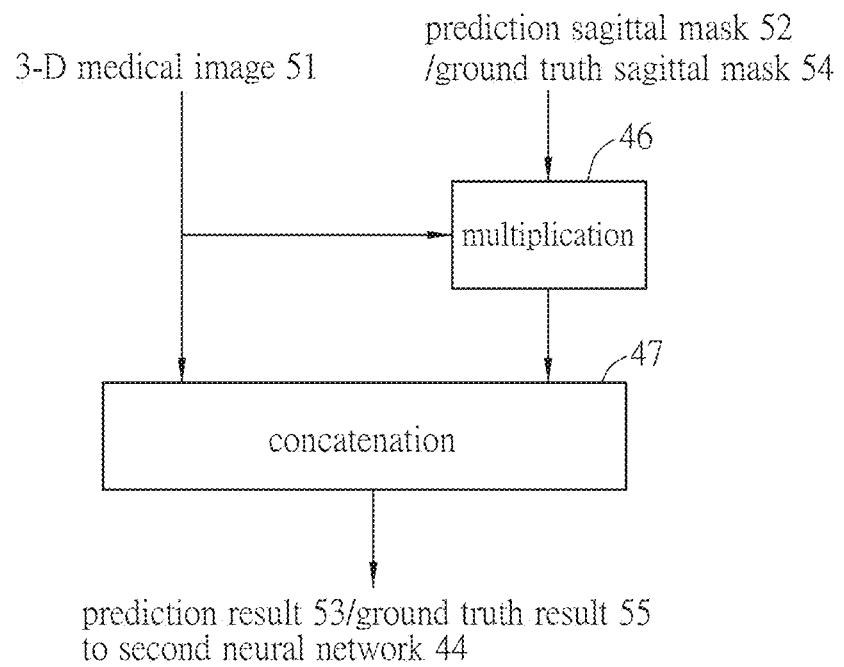
FIG. 2B is a block diagram showing the combining calculation according to an embodiment of this disclosure.

Referring to FIG. 2B, the prediction result generation 42 and the ground truth result generation 43 can have the same combining calculation. That is, the program code of the combining calculation can be used in the prediction result generation 42 and the ground truth result generation 43. As shown in FIG. 2B, the combining calculation comprises a multiplication 46 and a concatenation 47. Before the data is sent to the second neural network 44, the 3-D mask and the 3-D medical image 51 are provided to the combining calculation, and the combining calculation includes an element-wise multiplication, which is configured for retrieving the intensity plane from the original 3-D medical image 51. Next, the result of the multiplication 46 and the 3-D medical image 51 are provided to the concatenation 47. The output of the concatenation 47 is a two-channel data and sent to the second neural network 44.

In the prediction result generation 42, the 3-D mask is the prediction sagittal mask 52, and the output of the concatenation 47 is the prediction result 53. In the ground truth result generation 43, the 3-D mask is the ground truth sagittal mask 54, and the output of the concatenation 47 is the ground truth result 55.

Referring to FIG. 2A, the second neural network 44 takes the prediction result 53 and the ground truth result 55 as the input and processes them, and the processing result is inputted to the loss function calculation 45. In the loss function calculation 45, the loss function data 56 and 57 comprise the first loss function data 56 and the second loss function data 57. The first loss function data 56 is used for adjusting the first neural network 41, and the second loss function data 57 is used for adjusting the second neural network 44.

The filter weights of the first neural network 41 and the second neural network 44 can be trained with utilizing the loss function data 56 and 57. In the case of generative adversarial network, the loss function can be WGAN-GP, or a modified version based on WGAN-GP. The loss function data 56 and 57 can be generated according to the following functions:

$$L^{ce} = wE[-y \log(x) - (1-y)\log(1-x)]$$

$$L^G = -(1-w)(E[C(x')]) + L^{ce}$$

$$L^C = E[C(x')] - E[C(y')] + \lambda E[(\|\nabla_{\hat{x}} C(\hat{x}')\|_2 - 1)^2]$$

Figure 2C:
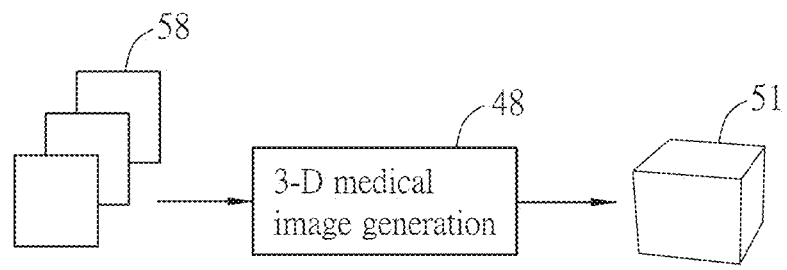
FIG. 2C is a block diagram of generating the 3-D medical image according to an embodiment of this disclosure.

$L^G$: loss function for updating generator
$L^C$: loss function for updating critic
$L^{ce}$: cross entropy
x: prediction sagittal mask
y: ground truth sagittal mask
$\hat{x}$: a linear function of x and y with random weight, $\hat{x} = \alpha y + (1-\alpha)x$
α: random weight, $\alpha \in (0,1)$
x': prediction result
y': ground truth result
$\hat{x}'$: a linear function of x' and y' with random weight, $\hat{x}' = \alpha y' + (1-\alpha)x'$
C: critic
E: expectation
λ: weight of gradient penalty
w: weight, for controlling the balance of the cross entropy loss and the adversarial loss FIG. 2C is a block diagram of generating the 3-D medical image according to an embodiment of this disclosure. As shown in FIG. 2C, the 3-D medical image generation 48 can create the 3-D medical image 51 of FIG. 2A according to a plurality of 2-D medical images 58. For example, the 2-D medical image 58 can be a 2-D ultrasound image, and the 3-D medical image 51 can be a 3-D ultrasound image. The program code and information for implementing the 3-D medical image generation 48 can be stored in the storage unit 22 of FIG. 1, and the processing core 21 can execute and process the program code and information.

Figure 3:
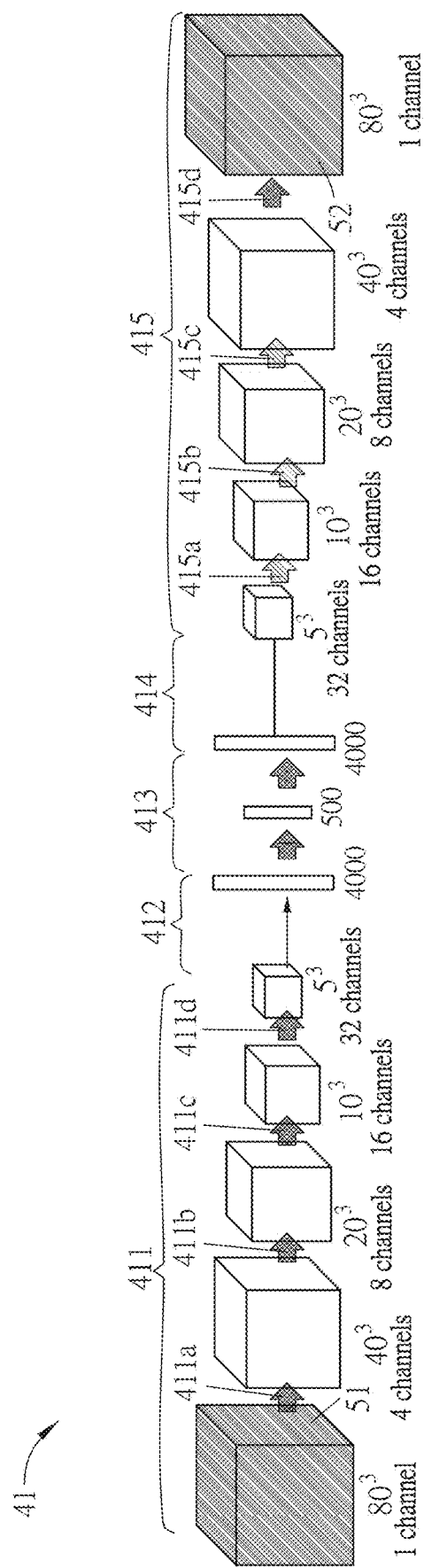
FIG. 3 is a schematic diagram showing the first neural network according to an embodiment of this disclosure.

FIG. 3 is a schematic diagram showing the first neural network according to an embodiment of this disclosure. As shown in FIG. 3, the first neural network 41 can be, for example, a convolutional neural network, which comprises a plurality of convolution layers 411, a flatten layer 412, a reshaping layer 414, and a plurality of deconvolution layers 415. The front half of the first neural network 41 can function as a coder, and the rear half of the first neural network 41 can function as a decoder. For example, the convolution layers 411 and the flatten layer 412 can function as a coder, and the reshaping layer 414 and the deconvolution layers 415 can function as a decoder. The final output of the deconvolution layers 415 can be the prediction sagittal mask 52.

For example, the convolutional neural network comprises four convolution layers 411. Each convolution layer 411 uses a kernel of the same size and has a stride of the same size (e.g. a 3×3×3 kernel and a 1×1×1 stride). The kernel can also be called as a filter. The thickness of the feature map is referred to as a channel, and the number thereof is gradually increased with the number of layers of the convolution layers 411. For example, the number of the channels of any consequent convolution layer will be a multiple of that of the previous one convolution layer 411 (after the first convolution layer 411a). As shown in FIG. 3, the number of input channel of the first convolution layer 411a is 1, and then the numbers of output channels from the first to fourth convolution layers 411a to 411d will be 4, 8, 16, and 32. The amount of data is changed to $80^3$, $40^3$, $20^3$, $10^3$, and $5^3$ in order. In other embodiments, the convolution layers 411 may have different sized kernels, or only a part of the convolution layers 411 have the same sized kernel (not all convolution layers 411 have the same sized kernel). In addition, the convolution layers 411 can also have different sized strides, respectively, or only a part of the convolution layers 411 have the same sized stride (not all of the convolution layers 411 have the same sized stride). The number of channels can also be changed in other ways, and is not limited to the above-mentioned multiplication.

The output of the convolution layer 411 can be further processed before entering the next convolution layer 411 or the flatten layer 412. For example, the output can be further processed with a ReLU layer (Rectified Linear Units layer) or a pooling layer. The ReLU layer utilizes, for example, a leaky ReLU function, and the pooling layer is, for example, a max pooling layer. For example, the output of each convolution layer 411 can be processed by the ReLU layer and the max pooling layer and then entered the next convolution layer 411, and the output of the last convolution layer 411 is sent to the flatten layer 412. Each ReLU layer utilizes the leaky ReLU function, and each pooling layer is the max pooling layer (2×2×2 kernel and 2×2×2 stride). In other embodiments, only the outputs of a part of the convolution layers 411 are further processed before entering the next convolution layer 411 or the flatten layer 412 (not all of the outputs of the convolution layers 411 are further processed with the ReLU layer or the pooling layer).

The flatten layer 412 may be followed by two fully connected layers 413 and then connected to the reshaping layer 414. The fully connected layer 413 may also have a ReLU layer, for example, using a leaky ReLU function. The deconvolution layer 415 is connected to the reshaping layer 414. The data amounts between the flatten layer 412 and the reshaping layer 414 are 4000, 500 and 4000.

For example, the convolutional neural network 41 comprises four deconvolution layers 415. Each deconvolution layer 415 uses a kernel of the same size and has a stride of the same size (e.g. a 3×3×3 kernel and a 2×2×2 stride). The number of the channels is gradually decreased with the number of layers of the deconvolution layers 415. For example, the number of the channels of any consequent deconvolution layer will be a demultiplication of that of the previous one deconvolution layer 415 (until the last deconvolution layer 415). As shown in FIG. 3, the number of input channels of the first deconvolution layer 415 is 32, and then the number of output channels from the first to fourth convolution layers 415a to 415d will be 32, 16, 8, and 4. The number of the output channel of the last deconvolution layer 415d is 1. The amount of data is changed to $5^3$, $10^3$, $20^3$, $40^3$, and $80^3$ in order. In other embodiments, the deconvolution layers 415 may have different sized kernels, or only a part of the deconvolution layers 415 have the same sized kernel (not all deconvolution layers 415 have the same sized kernel). In addition, the deconvolution layers 415 can also have different sized strides, respectively, or only a part of the deconvolution layers 415 have the same sized stride (not all of the deconvolution layers 415 have the same sized stride). The number of channels can also be changed in other ways, and is not limited to the above-mentioned demultiplication.

The output of the deconvolution layer 415 can be further processed before entering the next deconvolution layer 415. For example, the output can be further processed with a ReLU layer (Rectified Linear Units layer), which utilizes, for example, a leaky ReLU function. For example, the output of each deconvolution layer 415 (excluding the last deconvolution layer 415d) can be processed by the ReLU layer and then entered the next deconvolution layer 415. The last deconvolution layer 415d has a sigmoid layer, and each ReLU layer utilizes the leaky ReLU function. In other embodiments, only the outputs of a part of the deconvolution layers 415 are further processed before entering the next deconvolution layer 415 (not all of the outputs of the deconvolution layers 415 are further processed with the ReLU layer).

Figure 4:
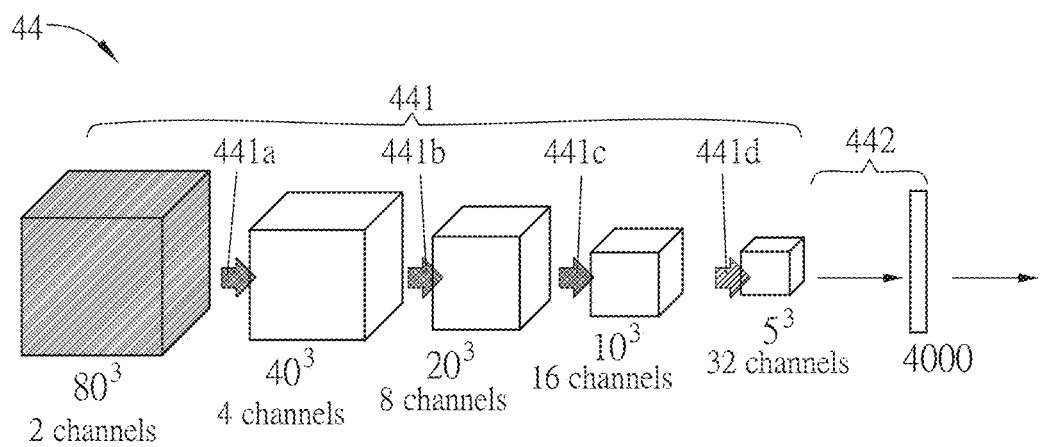
FIG. 4 is a schematic diagram showing the second neural network according to an embodiment of this disclosure.

FIG. 4 is a schematic diagram showing the second neural network according to an embodiment of this disclosure. As shown in FIG. 4, the architecture of the second neural network is similar to the coder of the first neural network. For example, the second neural network 44 can be a convolutional neural network, which comprises a plurality of convolution layers 441 and a flatten layer 442. The output of the flatten layer 442 can be provided to the loss function calculation.

For example, the convolutional neural network comprises four convolution layers 441. Each convolution layer 441 uses a kernel of the same size and has a stride of the same size (e.g. a 3×3×3 kernel and a 1×1×1 stride). The number of the channels is gradually increased with the number of layers of the convolution layers 441. For example, the number of the channels of any consequent convolution layer 441 will be a multiple of that of the previous one convolution layer 441 (after the first convolution layer 441a). As shown in FIG. 4, the number of input channels of the first convolution layer 441a is 2, and then the numbers of output channels from the first to fourth convolution layers 441a to 441d will be 4, 8, 16, and 32. The amount of data is changed to $80^3$, $40^3$, $20^3$, $10^3$, and $5^3$ in order. In other embodiments, the convolution layers 441 may have different sized kernels, or only a part of the convolution layers 441 have the same sized kernel (not all convolution layers 441 have the same sized kernel). In addition, the convolution layers 441 can also have different sized strides, respectively, or only a part of the convolution layers 441 have the same sized stride (not all of the convolution layers 441 have the same sized stride). The number of channels can also be changed in other ways, and is not limited to the above-mentioned multiplication.

The output of the convolution layer 441 can be further processed before entering the next convolution layer 441 or the flatten layer 442. For example, the output can be further processed with a ReLU layer (Rectified Linear Units layer), a sigmoid layer or a pooling layer. The ReLU layer utilizes, for example, a leaky ReLU function, and the pooling layer is, for example, a max pooling layer. For example, the output of each of the convolution layers 441a-441c (excluding the last convolution layer 441d) can be processed by the ReLU layer and the max pooling layer and then entered the next convolution layer 441b-441d, and the output of the last convolution layer 441d is processed by the sigmoid layer and the max pooling layer, and then sent to the flatten layer 442. Each ReLU layer utilizes the leaky ReLU function, and each pooling layer is the max pooling layer (2×2×2 kernel and 2×2×2 stride). In other embodiments, only the outputs of a part of the convolution layers 441 are further processed before entering the next convolution layer 441 or the flatten layer 442 (not all of the outputs of the convolution layers 441 are further processed with the ReLU layer, the sigmoid layer or the pooling layer). The final output of the second neural network 44 can be a latent vector instead of a value, so that it can represent the distribution of the true or false masks. As shown in FIG. 4, the amount of data after the flatten layer 442 is 4000.

Figure 5:
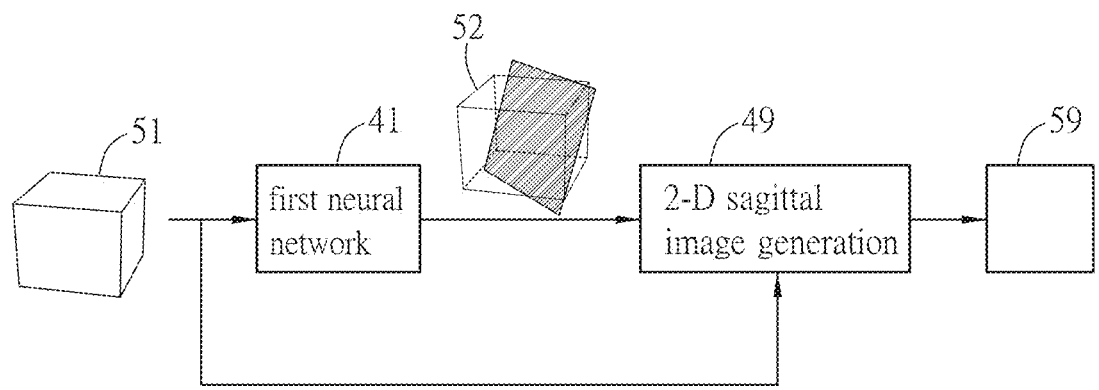
FIG. 5 is a block diagram showing a method of obtaining a medical sagittal image according to an embodiment of this disclosure.

FIG. 5 is a block diagram showing a method of obtaining a medical sagittal image according to an embodiment of this disclosure. As shown in FIG. 5, the first neural network 41, which is treated by the above-mentioned training method, can be used to obtain the medical sagittal image. The related implements and modifications of the first neural network 41 and the 3-D medical image 51 can be referred to the above descriptions. The program codes and information for implementing the first neural network 41 and the 2-D sagittal image generation 49 can be stored in the storage unit 22 of FIG. 1, and the processing core 21 can execute and process the program codes and information. The 3-D medical image 51, the prediction sagittal mask 52, and the sagittal image 59 can be stored in or loaded into the storage unit 22, and provided for the processing step of the processing core 21.

The first neural network 41 is used on the 3-D medical image 51 to generate the prediction sagittal mask 52. The 2-D sagittal image generation 49 can generate the 2-D sagittal image 59 according to the prediction sagittal mask 52 and the 3-D medical image 51. For example, the step of generating the 2-D sagittal image comprises: generating a sagittal description data according to the prediction sagittal mask 52; and converting a coordinate of the 3-D medical image 51 according to the sagittal description data to generate the 2-D sagittal image 59. The sagittal description data are, for example, a plane representation function of 3-D space.

Figure 6:
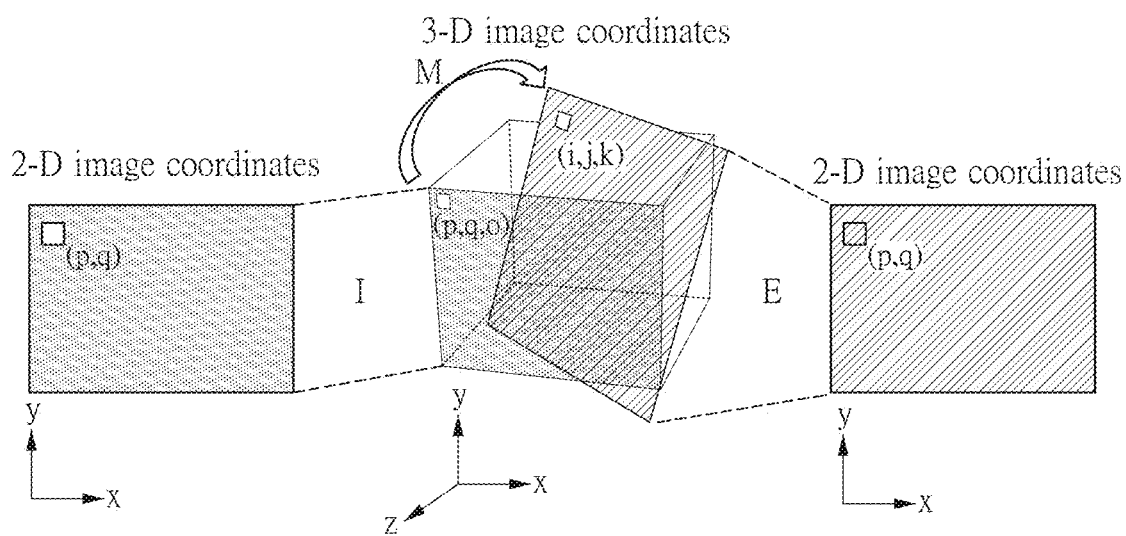
FIG. 6 is a schematic diagram showing the image coordinate conversion according to an embodiment of this disclosure.

FIG. 6 is a schematic diagram showing the image coordinate conversion according to an embodiment of this disclosure. As shown in FIG. 6, I indicates the initial sagittal plane, and the plane representation function thereof is z=0. The normal vector P of the initial sagittal plane I is (0, 0, 1). In the prediction sagittal mask 52, the RANSAC (RANdom SAmple Consensus) calculation is applied to a non-zero voxel for obtaining a result plane E (ax+by +cz+d=0). The normal vector Q of the result plane E is (a, b, c) (wherein, $a^2+b^2+c^2=1$).

M represents the relative transformation of each pixel between the initial sagittal plane I and the result plane E. In order to convert the coordinate position of each pixel (p, q) of the initial sagittal plane I in the 2-D image coordinates (i.e. the coordinate position of the voxel (p, q, 0) of the initial sagittal plane I in the 3-D image coordinates) to the coordinate position of the voxel (i, j, k) of the result plane E, the strength values of the coordinate position of the voxel (i, j, k) can be mapping onto the coordinate position of the corresponding pixel (p, q) of the result plane E. Then, the final 2-D image can be formed on the result plane E, so the 2-D image can be record as a 2-D format. The transformation M comprises a rotation matrix R and a translation matrix T (M=TR), and a 2-D sagittal image 59 can be obtained by calculation of the rotation matrix R and the translation matrix T.

For the normal vector P and the normal vector Q, the rotation angle θ and the rotation axis u can be obtained from the following calculation of the inner product and the outer product:

$$\theta = \arccos\left(\frac{P \cdot Q}{|P||Q|}\right)$$

$$u = \frac{P \times Q}{|P \times Q|}$$

According to Rodrigues' rotation formula, the rotation matrix R that is rotated by the rotation angle θ about the rotation axis u can be derived from the following equations, where the rotation axis u is expressed as $u=(u_x, u_y, u_z)$:

$$R = I + (\sin\theta)K + (1-\cos\theta)K^2 =$$

$$\begin{bmatrix} \cos\theta + u_x^2(1-\cos\theta) & u_x u_y(1-\cos\theta) - u_z\sin\theta & u_x u_z(1-\cos\theta) + u_y\sin\theta \\ u_y u_x(1-\cos\theta) + u_z\sin\theta & \cos\theta + u_y^2(1-\cos\theta) & u_y u_z(1-\cos\theta) - u_x\sin\theta \\ u_z u_x(1-\cos\theta) - u_y\sin\theta & u_z u_y(1-\cos\theta) + u_x\sin\theta & \cos\theta + u_z^2(1-\cos\theta) \end{bmatrix}$$

$$K = \begin{bmatrix} 0 & -u_z & u_y \\ u_z & 0 & -u_x \\ -u_y & u_x & 0 \end{bmatrix}$$

$$\|K\|_2 = 1$$

The parameter d of the translation matrix T is the offset from the original position. Starting from the initial point (x, y, z), the new point (x', y', z') can be arrived after d times along the unit normal vector Q=(a,b,c). The translation matrix T can be derived from the following equation:

$$\begin{bmatrix} x' \\ y' \\ z' \\ 1 \end{bmatrix} = \begin{bmatrix} x + ad \\ y + bd \\ z + cd \\ 1 \end{bmatrix} = \begin{bmatrix} 1 & 0 & 0 & ad \\ 0 & 1 & 0 & bd \\ 0 & 0 & 1 & cd \\ 0 & 0 & 0 & 1 \end{bmatrix} \begin{bmatrix} x \\ y \\ z \\ 1 \end{bmatrix} = T \begin{bmatrix} x \\ y \\ z \\ 1 \end{bmatrix}$$

Figure 7A:
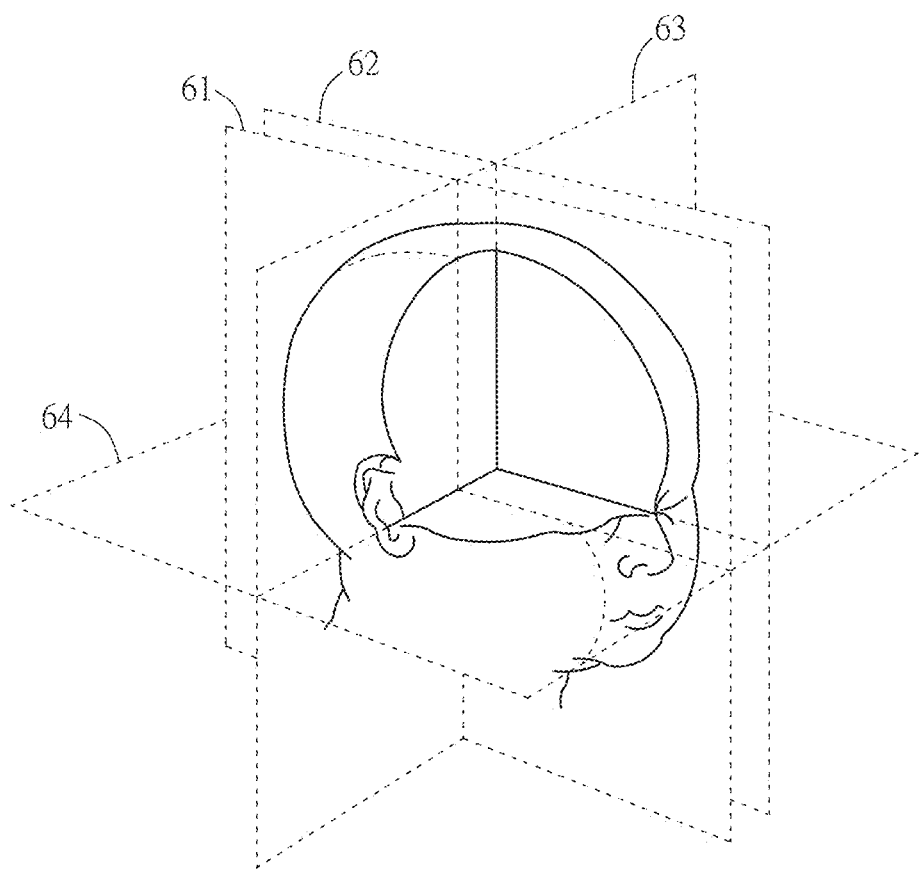
FIG. 7A is a schematic diagram showing the sagittal plane according to an embodiment of this disclosure.

FIG. 7A is a schematic diagram showing the sagittal plane according to an embodiment of this disclosure. The reference number 61 represents the sagittal plane, the reference number 62 represents the median plane, the reference number 63 represents the coronal plane, and the reference number 64 represents the horizontal plane.

Figure 7B:
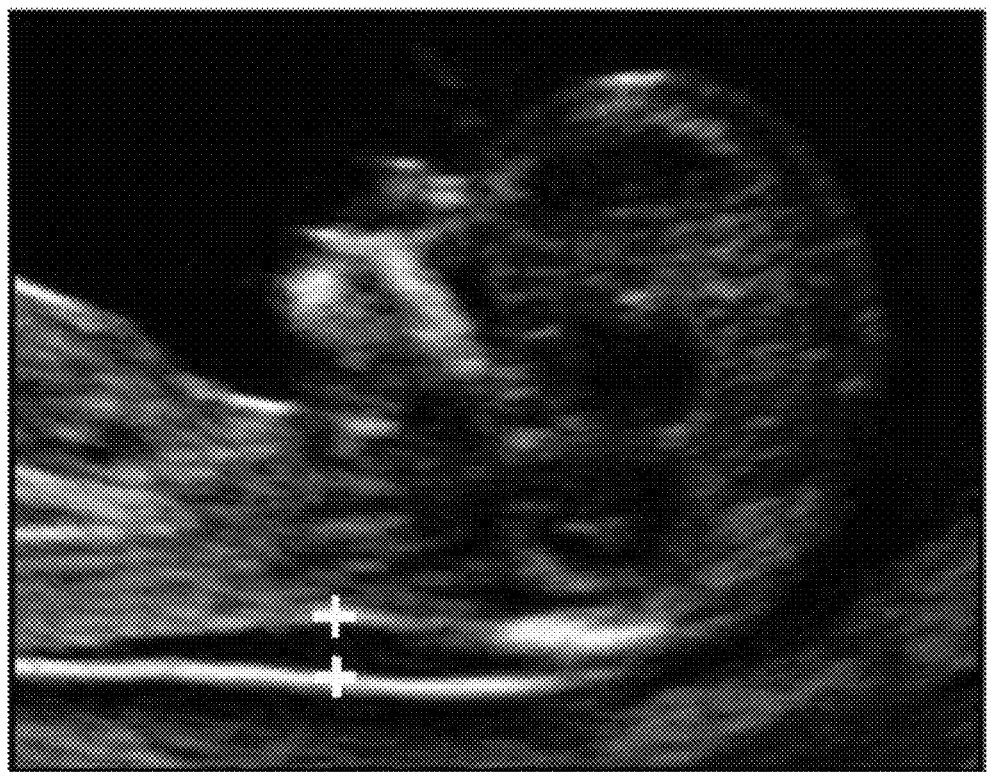
FIGS. 7B to 7D are schematic diagrams showing the ultrasound images of the medical sagittal image.
Figure 7C:
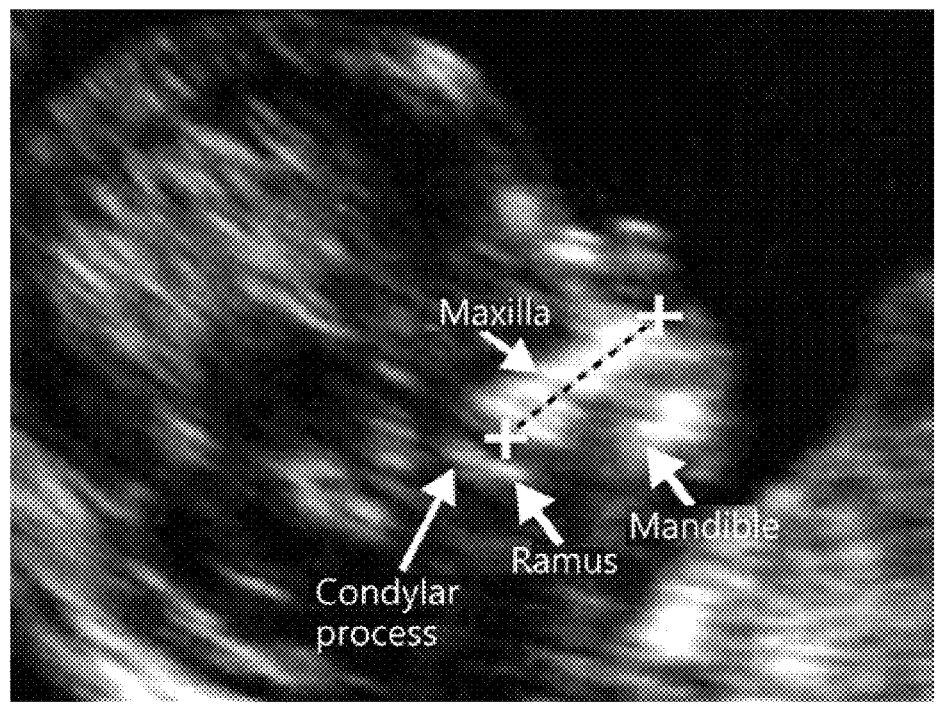
Figure 7D:
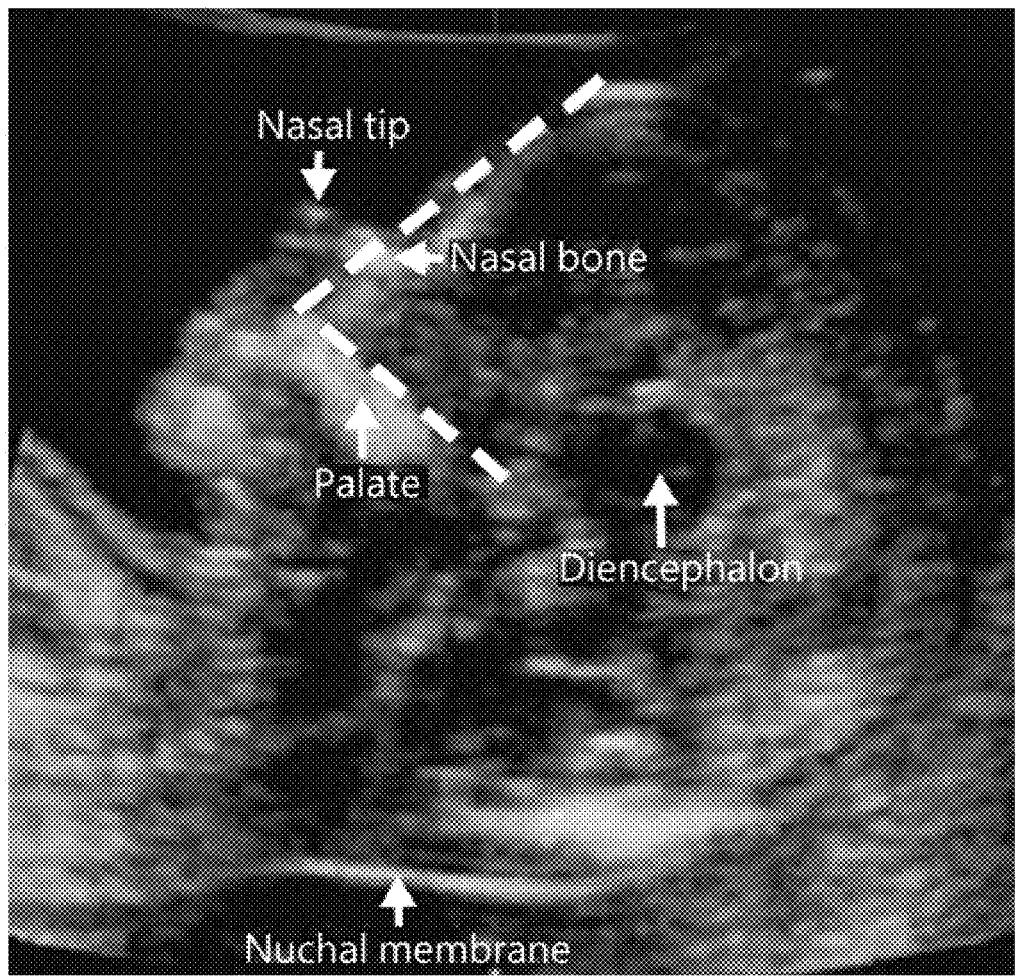

FIGS. 7B to 7D are schematic diagrams showing the ultrasound images of the medical sagittal image. The ultrasonic scanning has the advantages of low cost, immediate and non-invasive detection, and can be used for prenatal detection. During the first trimester, the obstetrician will measure the growth sputum based on the fetal middle sagittal plane (MSP), such as the nuchal translucency thickness (NTT), the maxillary length, and the frontomaxillary facial angle (FMF angle) to evaluate whether the fetus has chromosomal abnormalities and stunting. By using the above obtaining method, the middle sagittal plane of the fetal 3-D ultrasound image can be automatically detected so as to generate a 2-D sagittal image. FIG. 7B shows the measurement result of the thickness of the neck transparent strip, FIG. 7C shows the measurement result of the length of the upper tibia, and FIG. 7D shows the measurement result of the angle between the upper tibia and the frontal bone.

To sum up, in the method of training a neural network for obtaining a medical sagittal image, the method of obtaining a medical sagittal image, and the computing device of this disclosure, the neural network is used for detecting the sagittal plane (e.g. the middle sagittal plane (MSP) of fetal from the ultrasound image). The neural network can be used as a filter for learning the feature points in the medical image and the spatial position thereof, and generating a 3-D mask containing the plane position information. After the post-processing (conversion), the desired image of the middle sagittal plane can be obtained.

Although the disclosure has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the disclosure.

What is claimed is:

1. A method of training a neural network for obtaining a medical sagittal image, comprising:
    using a first neural network on a 3-D medical image for learning feature points in the 3-D medical image and a spatial position thereof to generate a prediction sagittal mask containing plane position information;
    generating a prediction result according to the 3-D medical image and the prediction sagittal mask;
    generating a ground truth result according to the 3-D medical image and a ground truth sagittal mask;
    using a second neural network on the prediction result and the ground truth result;
    generating a loss function data according to an output of the second neural network; and
    adjusting parameters of the first neural network or the second neural network according to the loss function data,
    wherein the prediction result is generated according to a combining calculation of the 3-D medical image and the prediction sagittal mask, and the ground truth result is generated according to a combining calculation of the 3-D medical image and the ground truth sagittal mask.

2. The method according to claim 1, wherein the 3-D medical image is an ultrasound image, a computed tomography image, a panoramic X-ray image, or a magnetic resonance image.

3. The method according to claim 1, wherein the first neural network is a convolutional neural network comprising a plurality of convolution layers, a flatten layer, a reshaping layer, and a plurality of deconvolution layers.

4. The method according to claim 1, wherein the second neural network is a convolutional neural network comprising a plurality of convolution layers and a flatten layer.

5. The method according to claim 1, wherein the loss function data comprises:
    a first loss function data for adjusting the first neural network; and
    a second loss function data for adjusting the second neural network.

6. The method according to claim 1, wherein the first neural network and the second neural network are a generative adversarial network.

7. The method according to claim 1, further comprising:
    creating the 3-D medical image according to a plurality of 2-D medical images.

8. The method according to claim 1, further comprising:
    generating a 2-D sagittal image according to the prediction sagittal mask and the 3-D medical image.

9. A method of obtaining a medical sagittal image, comprising:
    using a first neural network on a 3-D medical image for learning feature points in the 3-D medical image and a spatial position thereof to generate a prediction sagittal mask containing plane position information; and
    generating a 2-D sagittal image according to the 3-D medical image and the prediction sagittal mask,
    wherein the first neural network is a neural network treated by the method of training the neural network according to claim 1.

10. The method according to claim 9, wherein the step of generating the 2-D sagittal image comprises:
generating a sagittal description data; and
converting a coordinate of the 3-D medical image according to the sagittal description data to generate the 2-D sagittal image.

11. The method according to claim 9, wherein the 3-D medical image is an ultrasound image, a computed tomography image, a panoramic X-ray image, or a magnetic resonance image.

12. The method according to claim 9, wherein the first neural network is a convolutional neural network comprising a plurality of convolution layers, a flatten layer, a reshaping layer, and a plurality of deconvolution layers.

13. The method according to claim 9, further comprising:
creating the 3-D medical image according to a plurality of 2-D medical images.

14. A computing device performing a method of training a neural network for obtaining a medical sagittal image, wherein the method comprises:
using a first neural network on a 3-D medical image for learning feature points in the 3-D medical image and a spatial position thereof to generate a prediction sagittal mask containing plane position information;
generating a prediction result according to the 3-D medical image and the prediction sagittal mask;
generating a ground truth result according to the 3-D medical image and a ground truth sagittal mask;
using a second neural network on the prediction result and the ground truth result;
generating a loss function data according to an output of the second neural network; and
adjusting parameters of the first neural network or the second neural network according to the loss function data,
wherein the prediction result is generated according to a combining calculation of the 3-D medical image and the prediction sagittal mask, and the ground truth result is generated according to a combining calculation of the 3-D medical image and the ground truth sagittal mask.

* * * * *